United States Patent
Qu et al.

(10) Patent No.: US 9,425,253 B2
(45) Date of Patent: Aug. 23, 2016

(54) PASSIVATED NANOPARTICLES

(75) Inventors: Lianhua Qu, Pittsburgh, PA (US); Gregory Miller, Sunnyvale, CA (US)

(73) Assignee: Crystalplex Corporation, Pittsburgh, PA (US)

( * ) Notice: Subject to any disclaimer, the term of this patent is extended or adjusted under 35 U.S.C. 154(b) by 890 days.

(21) Appl. No.: 13/497,944

(22) PCT Filed: Sep. 23, 2010

(86) PCT No.: PCT/US2010/049988
§ 371 (c)(1),
(2), (4) Date: Oct. 26, 2012

(87) PCT Pub. No.: WO2011/038111
PCT Pub. Date: Mar. 31, 2011

(65) Prior Publication Data
US 2013/0039859 A1   Feb. 14, 2013

Related U.S. Application Data

(60) Provisional application No. 61/244,909, filed on Sep. 23, 2009.

(51) Int. Cl.
*H01L 23/29* (2006.01)
*A61K 9/14* (2006.01)
(Continued)

(52) U.S. Cl.
CPC ...... *H01L 29/0665* (2013.01); *A61K 47/48861* (2013.01); *A61K 49/0093* (2013.01); *B82Y 10/00* (2013.01); *B82Y 30/00* (2013.01); *B82Y 40/00* (2013.01); *C09K 11/025* (2013.01); *C09K 11/565* (2013.01); *C09K 11/883* (2013.01); *G01N 33/533* (2013.01); *G01N 33/588* (2013.01); *H01L 23/291* (2013.01); *H01L 23/3171* (2013.01); *H01L 29/127* (2013.01); *H01L 29/221* (2013.01); *H01L 29/2203* (2013.01); *A61K 9/14* (2013.01); *H01L 21/02406* (2013.01); *H01L 21/02409* (2013.01); *H01L 21/02521* (2013.01); *H01L 21/02557* (2013.01); *H01L 21/02601* (2013.01); *H01L 21/02628* (2013.01); *H01L 21/02664* (2013.01); *H01L 33/44* (2013.01); *H01L 2924/0002* (2013.01); *H01L 2924/12044* (2013.01);
(Continued)

(58) Field of Classification Search
None
See application file for complete search history.

(56) References Cited

U.S. PATENT DOCUMENTS 5,260,124 A   11/1993   Gaier
5,763,085 A   6/1998    Atarashi et al.
(Continued)

FOREIGN PATENT DOCUMENTS

EP   1790686 A2   5/2007
WO   2005001889 A1   1/2005
(Continued)

OTHER PUBLICATIONS

J Xu, J Xia, J Wang, J Shinar, Z Lin. "Quantum Dots Confined in Nanoporous Alumina Membranes." Applied Physics Letters, vol. 89, 2006, pp. 133110-1 to 133110-3 (3 total pages).*
(Continued)

*Primary Examiner* — Isaac Shomer
(74) *Attorney, Agent, or Firm* — Pepper Hamilton LLP

(57) ABSTRACT

Passivated semiconductor nanoparticles and methods for the fabrication and use of passivated semiconductor nanoparticles is provided herein.

17 Claims, 5 Drawing Sheets

(51) Int. Cl.

| | |
|---|---|
| H01L 29/06 | (2006.01) |
| B82Y 10/00 | (2011.01) |
| H01L 23/31 | (2006.01) |
| B82Y 30/00 | (2011.01) |
| B82Y 40/00 | (2011.01) |
| G01N 33/533 | (2006.01) |
| G01N 33/58 | (2006.01) |
| H01L 29/12 | (2006.01) |
| H01L 29/22 | (2006.01) |
| H01L 29/221 | (2006.01) |
| C09K 11/02 | (2006.01) |
| C09K 11/56 | (2006.01) |
| C09K 11/88 | (2006.01) |
| A61K 47/48 | (2006.01) |
| A61K 49/00 | (2006.01) |
| H01L 21/02 | (2006.01) |
| H01L 33/44 | (2010.01) |

(52) U.S. Cl.
CPC .......... Y10S 977/773 (2013.01); Y10S 977/906 (2013.01); Y10S 977/915 (2013.01); Y10S 977/927 (2013.01)

(56) References Cited

U.S. PATENT DOCUMENTS

| | | | |
|---|---|---|---|
| 6,057,396 | A | 5/2000 | Lan et al. |
| 6,322,901 | B1 | 11/2001 | Bawendi et al. |
| 6,423,551 | B1 | 7/2002 | Weiss et al. |
| 6,607,829 | B1 | 8/2003 | Bawendi et al. |
| 6,699,723 | B1 | 3/2004 | Weiss et al. |
| 6,821,337 | B2 | 11/2004 | Bawendi et al. |
| 6,861,155 | B2 | 3/2005 | Bawendi et al. |
| 6,927,069 | B2 | 8/2005 | Weiss et al. |
| 7,125,605 | B2 | 10/2006 | Bawendi et al. |
| 7,138,098 | B2 | 11/2006 | Bawendi et al. |
| 7,825,405 | B2 | 11/2010 | Kim et al. |
| 2001/0023078 | A1* | 9/2001 | Bawendi et al. ............. 436/524 |
| 2006/0028882 | A1* | 2/2006 | Qu .......................... 365/189.07 |
| 2006/0036084 | A1 | 2/2006 | Qu |
| 2006/0040103 | A1 | 2/2006 | Whiteford et al. |
| 2007/0087197 | A1 | 4/2007 | Jang et al. |
| 2007/0111324 | A1* | 5/2007 | Nie et al. ..................... 436/518 |
| 2008/0280161 | A1 | 11/2008 | Jang et al. |
| 2008/0296534 | A1 | 12/2008 | Lifshitz et al. |
| 2008/0311182 | A1 | 12/2008 | Ferrari et al. |
| 2009/0116753 | A1 | 5/2009 | Midgley et al. |
| 2009/0321692 | A1 | 12/2009 | LoCascio et al. |
| 2010/0167011 | A1 | 7/2010 | Dubrow |
| 2013/0011339 | A1 | 1/2013 | Colvin et al. |
| 2014/0001405 | A1 | 1/2014 | Guo et al. |
| 2014/0005083 | A1 | 1/2014 | Malshe |
| 2014/0045323 | A1 | 2/2014 | Gonen Williams et al. |
| 2015/0268370 | A1 | 9/2015 | Johnston et al. |

FOREIGN PATENT DOCUMENTS

| | | |
|---|---|---|
| WO | WO 2006/051153 A2 | 5/2006 |
| WO | WO 2006/134599 A1 | 12/2006 |
| WO | WO 2009/020436 A1 | 2/2009 |
| WO | WO 2009/026396 A1 | 2/2009 |
| WO | WO 2011/038111 A1 | 3/2011 |
| WO | WO2013/039897 A2 | 3/2013 |
| WO | WO 2013/191655 A1 | 12/2013 |

OTHER PUBLICATIONS

JL van Hemmen, SBS Heil, JH Klootwijk, F Roozeboom, CJ Hodson, MCM van de Sanden, WMM Kessels. "Plasma and Thermal ALD of Al2O3 in a Commercial 200 mm ALD Reactor." Journal of the Electrochemical Society, vol. 154(7), 2007, pp. G165-G169.*
A Pourret, P Guyot-Sionnest, JW Elam. "Atomic Layer Deposition of ZnO in Quantum Dot Thin Films." Advanced Materials, vol. 21, 2009, pp. 232-235.*
K Lambert, J Dendooven, C Detavernier, Z Hens. "Embedding Quantum Dot Monolayers in Al2O3 Using Atomic Layer Deposition" Chemistry of Materials, vol. 23, 2011, pp. 126-128.*
Alivisatos, Perspectives on the Physical Chemistry of Semiconductor Nanocrystals, J. Phys. Chem., (Aug. 1, 1996), 100(31):13226-13239.
Eychmuller, Structure and Photophysics of Semiconductor Nanocrystals, J. Phys. Chem. B, (Jun. 21, 2000), 32:104(28):6514-6528.
Harrison et al., Investigation of Factors Affecting the Photoluminescence of Colloidally-Prepared HgTe Nanocrystals, J. Mater. Chem., (1999), 9:2721-2722.
Hines et al., Synthesis and Characterization of Strongly Luminescing ZnS-Capped CdSe Nanocrystals, J. Phys. Chem., (1996), 100(2):468-471 (Abstract).
Korgel et al., Controlled Synthesis of Mixed Core and Layered (Zn,Cd)S and (Hg,Cd)S Nanocrystals Within Phosphatidylcholine Vesicles, Langmuir, (Mar. 11, 2000), 16(8):3588-3594.
Micic et al., Size Dependent Spectroscopy of InP Quantum Dots, J. Phys. Chem. B, (Jun. 19, 1997), 101 (25):4904-4912.
Murray et al., Synthesis and Characterization of Nearly Monodisperse CdE (E=S, Se, Te) Semiconductor Nanocrystallites, J. Am. Chem. Soc. (1993), 115(19):8706-8715.
Nirmal et al., Luminescence Photphysics in Semiconductor Nanocrystals, Acc. Chem. Res., (Nov. 25, 1999), 32(5):407-414.
Talapin et al., A Novel Organometallic Synthesis of Hihgly Luminescent CdTe Nanocrystals, J. Phys. Chem. B, (Mar. 22, 2001), 105(12):2260-2263.
PCT/US2012/043391 International Search Report dated Oct. 29, 2012.
Kanemitsu et al., Excitions in silicon quantum structures, *Journal of Luminescence*, (1999), 83-84:283-290.
Panigrahi et al., ZnO-SiO2 core-shell nanorod composite: Microstructure, emission and photoconductivity properties, *Chemical Physics Letters 511*, (2011), 91-96.
Van Hemmen et al., Plasma and Thermal ALD of $Al_2O_3$ in a Commercial 200 mm ALD Reactor, *Journal of the Electrochemical Society*, (2007), 154(7):G165-G169.
Veprek, Electronic and mechanical properties of nanocrystalline composites when approaching molecular size, *Thin Solid Films*, (1997), 145-153.
Supplementary European Search Report for EP 12801910 dated Nov. 12, 2014.
International Search Report and Written Opinion dated Aug. 5, 2015 for PCT/US2015/033288.
Chen et al., "ZnO/Al2O3 core-shell nanorod arrays: growth, structural characterization, and luminescent properties," *Nanotechnology IOP*, Bristol, GB (May 6, 2009), 20(18):185605.
Extended European Search Report issued on European Patent Application No. 10819454.9 dated Feb. 26, 2016.
Law, et al., "ZnO-$Al_2O_3$ and ZnO-$TIO_2$Core-Shell Nanowire Dye-Sensitized Solar Cells," *J. Phys. Chem, B. Materials, Survaces, Interfaces and Biophysical*, Washington DC, US (Nov. 16, 2006), 110(45):22652-22663.

* cited by examiner

PASSIVATED NANOPARTICLES

This application is a U.S. national phase application under 35 U.S.C. §371 of International Application No. PCT/US2010/049988, filed Sep. 23, 2010, which claims the benefit of and priority to U.S. Provisional Patent Application No. 61/244,909 filed Sep. 23, 2009, which is hereby incorporated by reference in its entirety.

FIELD

The invention relates to the field of semiconductor nanocrystals and methods of making and using them. More particularly, the invention relates to passivated semiconductor nanocrystals and methods of making and using them.

BACKGROUND

Semiconductor nanocrystals, also called quantum dots, are a unique type of nanoparticle, which exhibit size-dependent properties that are not observed in either their discrete atom or bulk phase counterparts. These properties include, for example, narrow, tunable emission spectra, enhanced magnetic properties, altered electrical or optical activity, altered chemical or biological activity, and extended fluorescence lifetimes and enhanced emission and photostability relative to traditional organic fluorophores. Semiconductor nanocrystals are currently under investigation for applications in fundamental scientific research efforts to potential applications in the optoelectronics, high-density memory, lasing media, solar cell, and biolabeling industries, among others.

Semiconductor nanocrystals of the prior art, while exhibiting remarkable and commercially relevant properties, are vulnerable to a number of degradation processes, such as for example, oxidation, hydration, or photo-ionization. Among these, are processes that directly attack the interior of the nanoparticles such as oxidation, and processes that attack or modify the surfaces of the nanoparticles. Interior-attack processes over time may irreparably modify the constituent materials and thereby eliminate their functionality altogether. Surface-attack and surface-modification processes result from interactions of the surfaces of the nanoparticles with surrounding media. For example, temperature, electrolyte concentration, and pH in surrounding aqueous media may contribute to nanocrystal degradation.

SUMMARY

Various embodiments of the invention are directed to a method for fabricating a passivated semiconductor nanocrystal, said method comprising the steps of: coating the surface of an alloy-gradient nanoparticle with an aluminum layer; and oxidizing the surface of said aluminum layer to form an aluminum oxide layer. In some embodiments, the oxidizing step includes exposing the aluminum layer to an ambient environment. In other embodiments, the oxidizing step includes exposing the aluminum layer to a controlled environment.

Certain embodiments of the invention are directed to a passivated semiconductor nanocrystal, prepared by a process comprising the steps of: synthesizing an alloy-gradient nanoparticle, said nanoparticle comprising at least one Group II element and two or more different Group VI elements; applying a binary semiconductor coating over said alloy-gradient nanoparticle, said coating having a wider band gap than the alloy-gradient nanoparticle; coating the surface of the binary semiconductor coated alloy-gradient nanoparticle with an aluminum layer; and oxidizing the surface of said aluminum layer by exposure to an ambient environment to form an aluminum oxide layer thereon, whereby a semiconductor nanocrystal of improved passivity is obtained. In some embodiments of the invention the alloy-gradient nanoparticle is homogenous and in others, the alloy-gradient nanoparticle is nonhomogeneous.

According to other embodiments of the invention, a passivated semiconductor nanocrystal is prepared by: synthesizing an alloy-gradient nanoparticle, said nanoparticle comprising at least one Group II element and two or more different Group VI elements; applying a binary semiconductor coating over said alloy-gradient nanoparticle, said coating having a wider band gap than the alloy-gradient nanoparticle; coating the surface of the binary semiconductor coated alloy-gradient nanoparticle with an aluminum layer; and oxidizing the surface of said aluminum layer by exposure to an ambient environment to form an aluminum oxide layer thereon, whereby a semiconductor nanocrystal of improved passivity is obtained. In certain embodiments, the synthesizing step may comprise dissolving the at least one Group II element and the two or more different Group VI elements in a solvent comprising octadecene and a fatty acid to provide a nanocrystal precursor solution and heating said precursor solution.

According to other embodiments of the invention, a passivated semiconductor nanocrystal is prepared by: synthesizing an alloy-gradient nanoparticle, said nanoparticle comprising at least one Group II element and two or more different Group VI elements; applying either a binary semiconductor coating or an alloy-gradient coating comprising at least one Group II element and two or more different Group VI elements over said alloy-gradient nanoparticle, said coating having a wider band gap than the alloy-gradient nanoparticle; coating the surface of the coated alloy-gradient nanoparticle with an aluminum layer; and oxidizing the surface of said aluminum layer by exposure to an ambient environment to form an aluminum oxide layer thereon, whereby a semiconductor nanocrystal of improved passivity is obtained. In certain embodiments, the synthesizing step may comprise dissolving the at least one Group II element and the two or more different Group VI elements in a solvent comprising octadecene and a fatty acid to provide a nanocrystal precursor solution and heating said precursor solution. In some embodiments, the semiconductor coating is a binary semiconductor coating. In some embodiments, the semiconductor coating is an alloy-gradient coating comprising at least one Group II element and two or more different Group VI elements.

In other embodiments of the invention, the method may further include the step of coupling an active agent to the passivated semiconductor nanocrystal. In some such embodiments, the active agent is associated with the surface of, encapsulated within, surrounded by, or dispersed throughout the passivated semiconductor nanocrystal. In particular embodiments of the invention, the active agent may be coupled to the aluminum oxide layer. In still other embodiments, the method may further include the step of coupling a targeting moiety to the passivated semiconductor nanocrystal. In particular embodiments, the targeting moiety may be coupled to the aluminum oxide layer. In other embodiments, the targeting moiety may be coupled to the active agent. In further embodiments of the invention, the method may include the step of coating said passivated semiconductor nanocrystal with an additional passivation material and in other embodiments, the method may include the step of coating said passivated semiconductor nanocrystal with a protective coating.

Other embodiments of the invention are directed to a method for passivating a semiconductor nanocrystal, said method comprising the steps of: applying a binary semiconductor coating over an alloy-gradient nanoparticle, said coating having a wider band gap than the alloy-gradient nanoparticle; coating the surface of the binary semiconductor coated alloy-gradient nanoparticle with an aluminum layer; and oxidizing the surface of said aluminum layer by exposure to an ambient environment to form an aluminum oxide layer thereon, whereby a semiconductor nanocrystal of improved passivity is obtained.

In certain embodiments of the invention, greater than 20% of the passivated semiconductor nanocrystal surface area is functionalized with the targeting moiety. In other embodiments, greater than 50% of the passivated semiconductor nanocrystal surface area is functionalized with the targeting moiety. In some embodiments, the passivated semiconductor nanocrystal has surface properties effective for extended circulation under physiological conditions.

Various embodiments of the invention are also directed to a method of diagnosing a disease in a subject, comprising administering to the subject an effective amount of a pharmaceutical composition comprising the passivated semiconductor nanocrystals of the invention. Other embodiments of the invention are directed to monitoring a biological process in vitro, said method comprising the steps of: dispensing the passivated semiconductor nanocrystal to a sample, wherein the targeting moiety specifically binds to a target in said sample and, wherein said target is integral to a biological process; and imaging the sample or a section thereof in response to a stimulus, thereby monitoring the biological process in vitro.

Other embodiments of the invention are directed to a method of monitoring a biological process in vivo, said method comprising the steps of: administering the passivated semiconductor nanocrystal to a subject, wherein the targeting moiety specifically binds to a target in the subject and, wherein said target is integral to a biological process; and imaging at least a portion of the subject, thereby monitoring the biological process in vivo.

BRIEF DESCRIPTION OF THE DRAWINGS

For a fuller understanding of the nature and advantages of the present invention, reference should be made to the following detailed description taken in connection with the accompanying figures, in which.

DETAILED DESCRIPTION

Figure 1A:
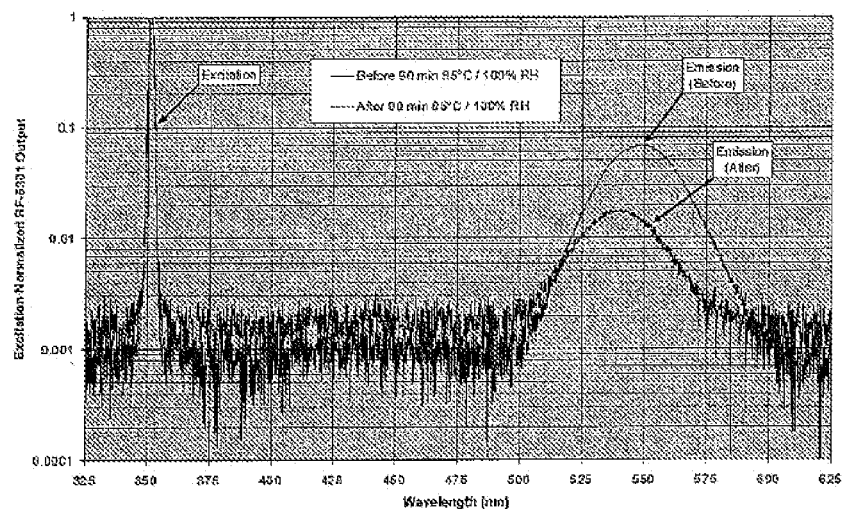
FIG. 1A is a log-scale excitation-normalized emission spectra of unpassivated quantum dots disclosed in prior art.

This invention is not limited to the particular compositions or methodologies described, as these may vary. In addition, the terminology used in the description describes particular versions or embodiments only and is not intended to limit the scope of the invention. Unless defined otherwise, all technical and scientific terms used herein have the same meanings as commonly understood by one of ordinary skill in the art. In case of conflict, the patent specification, including definitions, will prevail.

As used herein, the singular forms "a", "an" and "the" include plural reference unless the context clearly dictates otherwise.

As used herein, the term "about" means plus or minus 10% of the numerical value of the number with which it is being used. Therefore, about 50% means in the range of 40%-60%.

The terms "include", "comprise" and "have" and their conjugates, as used herein, mean "including but not necessarily limited to."

As used herein, the terms "nanoparticles", "nanocrystals", and "passivated nanocrystals" refer to small structures in which the ordinary properties of their constituent materials are altered by their physical dimensions due to quantum-mechanical effects, often referred to as "quantum confinement." For the sake of clarity, the use of the term "nanoparticles" in this disclosure refers to objects possessing quantum-confinement properties, which are separated from one another in all three dimensions; enabling incorporation into liquids, vapors, or solids.

"Optional" or "optionally" may be taken to mean that the subsequently described structure, event or circumstance may or may not occur, and that the description includes instances where the event occurs and instances where it does not.

In various embodiments of the invention, a passivation technique is provided whereby nanoparticles may be passivated and incorporated into a wide range of media without requiring the specialization or modification of nanoparticle design and fabrication methods.

Embodiments of the invention are directed to passivated semiconductor nanocrystals and methods of fabricating such passivated nanocrystals. In these embodiments, a passivation layer is formed on the outer layer of the nanoparticles. Passivation is a process in which a non-reactive layer is created on the surface of the nanoparticles. Without wishing to be bound by theory, the passivation layer may perform a quantum-mechanical function, including providing a tighter confinement of the quantum-mechanical wave functions, so that they do not extend beyond the surface of the passivation material. Passivation further enables the nanoparticles to be used in a wide variety of media and in a wide variety of applications.

Any passivation material known in the art may be utilized in the context of the present invention. The key criteria for achieving passivation in the context of this invention are the prevention of chemical contamination of the nanoparticle, the stability of the passivation material in the intended application, and the quantum-mechanical bandgap of the passivation material of sufficient magnitude to prevent undesired interaction of the nanoparticle's desired wave functions with the ambient chemical environment. For example, the passivation material may include aluminum, carbon, and silicon, to name a few. Aluminum is a preferred passivation material because it is well-known to aggressively scavenge oxygen to form aluminum oxide ($Al_2O_3$), and $Al_2O_3$, once formed, is a strong barrier to oxidation and other degradation processes. $Al_2O_3$ is also optically transparent and has a band gap for electrons and holes much greater than many of the semiconducting materials in the quantum dots themselves. In certain embodiments of the invention, one or more passivation materials may be utilized in one or more layers.

Various embodiments of the invention are directed to a method for fabricating a passivated semiconductor nanocrystal, said method comprising the steps of: coating the surface of an alloy-gradient nanoparticle with an passivation material, such as, for example, aluminum; and oxidizing the surface of said passivation material to form an oxide layer. In some embodiments, the oxidizing step includes exposing the passivation material to an ambient environment. In other embodiments, the oxidizing step includes exposing the passivation material to a controlled or engineered environment. In some embodiments, the passivation material may be completely oxidized while in other embodiments, the oxidation may be controlled so that only a few monolayers of the passivation material are oxidized.

The passivation techniques of the invention can be applied to a variety of nanoparticles known in the art. The passivated nanoparticles of embodiments of the invention may comprise, for example, core-shell, alloy or gradient structures of any material, such as a II-VI, IV-VI, or a III-V semiconductor material. In numerous embodiments, the nanoparticles comprise IV-VI or II-VI semiconductor nanoparticles, such as CdS, ZnS, PbS, CdSe, ZnSe, PbSe, ZnTe, PbTe and CdTe nanoparticles. In other embodiments, ternary and quaternary semiconductor nanoparticles, such as CdZnS, CdZnSe, CdSeS, CdZnTe, CdZnTeSe, and CdZnSSe, for example, may also be used. Some embodiments of the invention are directed to a semiconductor nanocrystal comprising an alloy or more than four elements. In addition, semiconductor nanoparticles other than IV-VI or II-VI nanoparticles may also be used. These nanoparticles include, for example, GaAs, GaP, GaN, InP, InAs, GaAlAs, GaAlP, GaAlN, GaInN, GaAlAsP, GaAlInN, and various other III-V materials.

Particular embodiments of the invention are directed to a passivated semiconductor nanocrystal comprising an alloyed-gradient nanocrystal. The term "alloyed", as used herein, means that the semiconductor materials comprising the quantum dot are capable of forming an amalgamated solid wherein the semiconductors are randomly distributed throughout the solid. Furthermore, one of ordinary skill in the art realizes that each of the at least two semiconductors of the alloyed semiconductor quantum dots is a different semiconductor from the other(s). Likewise, one of ordinary skill in the art realizes that each of the first semiconductor and second semiconductor of the alloyed-gradient quantum dot is different from the other. Alloyed-gradient quantum dots are generally more stable than conventional core-shell quantum dots. In part, the composition-gradient avoids the stresses and defects associated with abrupt material interfaces with the beneficial effect of slowing or suppressing the propagation of defects into the sensitive interior region of the particles.

The alloyed-gradient semiconductor nanocrystals of some embodiments of the invention have a homogeneous composition. As used herein, the term "homogeneous composition" means that the nanocrystal has a uniform composition throughout, such that the composition is the same with respect to the semiconductors comprising the nanocrystal and the molar ratio of the semiconductors comprising the nanocrystal, i.e., the nanocrystal is uniform in composition from its centerpoint to its surface. In other aspects, the alloyed-gradient semiconductor nanocrystals do not have a homogeneous composition. For example, in some embodiments, the concentration of a first semiconductor gradually increases from the centerpoint of the nanocrystal to the surface of the nanocrystal, while the concentration of a second semiconductor gradually decreases from the centerpoint of the nanocrystal to the surface of the nanocrystal.

In certain embodiments of the invention, the nanoparticles to be passivated can have a semiconductor shell, i.e., can be encapsulated within a shell comprising a semiconductor. The term "semiconductor shell", as used herein, refers to a thin layer of semiconductor material (typically 1-10 atomic layers thick) deposited on the outer surface of the nanoparticle; this "semiconductor shell" is composed of a different semiconductor material than the nanoparticle itself. By "different" it is meant that either the ratio of the elements and/or the choice of elements in the shell differs from that of the nanoparticle itself. In addition, the semiconductor shell should have a wider band gap than the nanoparticle core in order to efficiently protect the core electronically and sterically. The semiconductor shell can comprise any semiconductor known in the art, including, but not limited to binary semiconductor coatings, and coatings comprising at least one Group II element and two or more different Group VI elements. Some exemplary semiconductor coatings include, but are not limited to, CdS, ZnS, PbS, CdSe, ZnSe, PbSe, ZnTe, PbTe, CdTe, CdZnS, CdZnSe, CdZnTe, CdZnTeSe, CdZnSSe, GaAs, GaP, GaN, InP, InAs, GaAlAs, GaAlP, GaAlN, GaInN, GaAlAsP, GaAlInN, among others. Preferably, the semiconductor shell comprises ZnS, CdS, CdSe, CdTe, GaAs, or AlGaAs. Implementation of this core/shell structure, where a few monolayers of higher band gap semiconductor materials are epitaxialy grown on prepared nanoparticles, or "cores", have improved qualities regarding stability and photoluminescence quantum efficiency. In particular, the overcoating with a wider bandgap semiconductor protects the surface nonradiative sites, thereby improving the luminescence efficiency of the nanocrystal.

Various embodiments of the invention are directed to the application of aluminum coating onto alloy-gradient nanoparticles having a semiconductor shell and permitting such coating to reach full oxidation wherein the resultant $Al_2O_3$ passivation layer isolates the nanoparticles against their environment, and provides robust quantum confinement. In some embodiments, oxidation of the aluminum coating occurs at ambient temperature. In other embodiments, oxidation of the aluminum coating occurs at elevated temperature, such as, for example, 100° C. In certain aspects of the invention, the $Al_2O_3$ passivation layer comprises amorphous $Al_2O_3$.

The fabrication methods for the passivated nanocrystals of the invention may be further modified in some embodiments to achieve desired features. For example, nanoparticle characteristics such as surface functionality, surface charge, particle size, zeta ($\zeta$) potential, hydrophobicity, and the like, may be optimized depending on the particular application of the passivated nanocrystals. For example, in some embodiments of the invention, modified surface chemistry and small particle size may contribute to reduced clearance of the nanoparticles. In other embodiments, the passivated nanoparticles are stable in water or other liquid medium without substantial agglomeration and substantial precipitation for at least 30 days, preferably for at least 90 days, and more preferably for at least 120 days. The term "stable" or "stabilized" means a solution or suspension in a fluid phase wherein solid components (i.e., nanoparticles) possess stability against aggregation and agglomeration sufficient to maintain the integrity of the compound and preferably for a sufficient period of time to be useful for the purposes detailed herein. As used herein, the term "agglomeration" refers to the formation of a cohesive mass consisting of particulate subunits held together by relatively weak forces (for example, van der Waals or capillary forces) that may break apart into particulate subunits upon processing, for example. The resulting structure is called an "agglomerate."

The passivated nanocrystals of the invention can have any diameter, and, thus, be of any size, provided that quantum confinement is achieved. In certain embodiments, the passivated nanocrystals described herein have a primary particle size of less than about 10 nm in diameter. According to other embodiments, the passivated nanocrystals have a primary particle size of between about 1 to about 500 nm in diameter. In other embodiments, a primary particle size of between about 1 to about 100 nm in diameter, and in still other embodiments, a primary particle size of between about 5 to about 15 nm in diameter. As used herein, the phrase "primary particle" refers to the smallest identifiable subdivision in a particulate system. Primary particles can also be subunits of aggregates.

The passivated nanocrystals of embodiments of the invention may be applicable to a wide variety of applications. Without wishing to be bound by theory, the passivating layer may confine the wave function(s) to a large enough extent to enable the use of nanoparticle materials otherwise considered as having too low a bandgap energy for applications such as, for example, direct visible light generation from GaInAlP quaternary compounds. In another embodiment, the integration of passivating layer may also stabilize performance and manage quantum-mechanical wave functions, for applicability in optoelectronic, photoluminescent, photovoltaic, magnetic, and electroluminescent applications. As such, the passivated nanoparticles of embodiments of the invention may find application in polishing slurries, paints, coatings, inks, cleaning compositions, structural material, electronic devices, light-emitting devices, light-receiving devices, codes, tags, data storage, optical switch, photodetector, transmission grating, optical filter, sensors, and lighting applications, among others.

In certain embodiments, the passivated nanocrystals may be used in optoelectronic methods or as optoelectronic devices. For example, the passivated nanocrystals may be used in light-emitting diodes (LEDs), solid-state lighting, or organic LEDs across the visible, ultraviolet and infra red wavelengths. The passivated nanocrystals of the invention may also find application in solar cells. In some embodiments, the passivated nanocrystals may be arranged and deposited onto a substrate, such as, for example, in an array as a thin film or layers of thin films on a support substrate or as a coating on or around another electronic material. The support substrate and layered passivated nanocrystal film or other coated electronic material may be processed into bulk semiconductor materials having the unique properties of the passivated nanocrystals of the invention.

In addition, due to the superior photoemission and photostability characteristics, the passivated nanocrystals of the invention may be applicable in in vitro and in vivo biological and medical applications, such as, for example, bioimaging, drug delivery, and gene therapy. In such embodiments, the passivated nanocrystals prepared according to the methods of the invention may be formed as a pharmaceutical composition.

Particular embodiments of the invention are directed to a method of diagnosing and/or treating a disease in a patient, comprising administering to the patient an effective amount of such pharmaceutical compositions containing the passivated nanocrystals. "Treatment" and "treating" refer to administration or application of a pharmaceutical composition embodied in the invention to a subject or performance of a procedure or modality on a subject for the purpose of obtaining a therapeutic benefit of a disease or health-related condition. A "disease" or "health-related condition", as used herein, can be any pathological condition of a body part, an organ, or a system resulting from any cause, such as infection, genetic defect, and/or environmental stress. The cause may or may not be known. The present invention may be used to diagnose, treat or prevent any disease or health-related condition in a subject. Examples of such diseases may include, for example, infectious diseases, inflammatory diseases, hyperproliferative diseases such as cancer, degenerative diseases, and so forth. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. An "effective amount" or "therapeutically effective amount" of a composition, as used herein, is a predetermined amount calculated to achieve a desired effect.

In certain embodiments, pharmaceutical compositions containing the passivated nanocrystals may comprise more than one active ingredient, such as more than one type of passivated nanocrystal. The pharmaceutical composition may alternatively comprise a passivated nanocrystal in combination with one or more active agents. The passivated nanocrystal may be coupled to the active agent through any means, e.g., chemical bonds, electrostatic interactions, crosslinkers, and the like. In addition, the active agent may be associated with the surface of, encapsulated within, surrounded by, or dispersed throughout the passivated semiconductor nanocrystal. As used herein, the term "active agent" means a compound utilized to image, impact, treat, combat, ameliorate, prevent or improve an unwanted condition or disease of a patient. The term "patient", as used herein, refers to subjects to be treated including humans and other higher animals, and laboratory models, such as mice and rats. In another embodiment, one or more active agents may be conjugated to one or more types of passivated nanocrystals.

In some embodiments of the invention, targeting moieties may be selected to ensure that the passivated nanocrystals selectively attach to, or otherwise associate with, a selected marker or target. The term "target", as used herein, refers to the material for which imaging, deactivation, rupture, disruption or destruction is desired. Through functionalization of nanoparticle surfaces with such targeting moieties, the passivated nanocrystals are effective only at targeted sites, which minimizes adverse side effects and improves efficacy.

In some embodiments of the invention, a linker may be utilized. The term "linker" as used herein, refers to any agent or molecule that bridges the passivated nanocrystals to the targeting moiety. This linker may be removed from the nanoparticle by chemical means, by enzymatic means, or spontaneously. In some embodiments, the linker may be pharmacologically inert or may itself provide added beneficial pharmacological activity. The term "spacer" may also be used interchangeably as a synonym for linker. Linkers used in the present disclosure may include, for example, lipids, polypeptides, oligonucleotides, polymers, and the like. It is also within the scope of the invention that more than one linker may be used to attach a targeting moiety. For example, a first linker may be attached to a passivated nanocrystal followed by a second linker that is attached to the first linker A third linker may be attached to the second linker and so on and so forth. In addition, one linker may be attached to the passivated nanocrystal and one linker may be attached to the targeting moiety. In this embodiment, the two linkers are joined to form the linker.

In various embodiments, the passivated nanoparticles may be well-dispersed and unagglomerated, which may facilitate conjugation or functionalization of the passivated nanoparticle surfaces with targeting moieties. As used herein, the terms "unagglomerated", "nonaggregated", and "unagglomeration" refer to a state of dispersion in a suspension. In particular aspects of the present invention, the passivated nanocrystals may be optimized with a specific ratio of conjugated to non-conjugated nanoparticle surface area, such that an effective amount of targeting moiety is associated with the passivated nanocrystals. According to an embodiment of the invention, the portion of the surface area of the passivated nanoparticle functionalized with a targeting moiety is greater than 25% of the total surface area. According to another embodiment of the invention, the portion of the surface area of the passivated nanoparticle functionalized with a targeting moiety is greater than 50% of the total surface area. Increased density of the targeting moiety will generally increase target binding. Alternatively, an increase in non-conjugated nanoparticle surface area may influence inflammation, immunogenicity (i.e., the ability to provoke an immune response), and/or nanoparticle circulation half-life. Furthermore, an increase in non-conjugated nanoparticle surface area will typically lower the rate of clearance of the nanoparticles from the circulatory system via the reticuloendothelial system (RES).

Exemplary targeting moieties include, for example, proteins, peptides, antibodies, antibody fragments, saccharides, carbohydrates, glycans, cytokines, chemokines, nucleotides, lectins, lipids, receptors, steroids, neurotransmitters and combinations thereof. The choice of a marker may vary depending on the selected target, but in general, markers that may be useful in embodiments of the invention include, but are not limited to, cell surface markers, a cancer antigen (CA), a glycoprotein antigen, a melanoma associated antigen (MAA), a proteolytic enzyme, an angiogenesis marker, a prostate membrane specific antigen (PMSA), a small cell lung carcinoma antigen (SCLCA), a hormone receptor, a tumor suppressor gene antigen, a cell cycle regulator antigen, a proliferation marker, and a human carcinoma antigen. In other aspects of the invention, targeting moieties are targeted to an antigen associated with a disease of a patient's immune system or a pathogen-borne condition. In yet another aspect, targeting moieties are targeted to cells present in normal healthy conditions. Such targeting moieties may be directly targeted to a molecule or other target or indirectly targeted to a molecule or other target associated with a biological molecular pathway related to a condition.

In another embodiment of the invention, the passivated nanocrystals can be formulated into a depot. Depot formulations of passivated nanocrystals may include, for example, an implantable composition comprising the passivated nanocrystals and a porous material, wherein the passivated nanocrystals are encapsulated by or diffused throughout the porous material. The passivated nanocrystal depot may be positioned in a desired location affiliated with the patient's body upon which the nanoparticles may be released from the implant at a predetermined rate by diffusing through the porous material.

Once the passivated nanocrystals have been prepared and optionally functionalized, formulated or conjugated, they may be combined with an acceptable carrier to produce a pharmaceutical formulation, according to another aspect of the invention. The carrier can be any suitable carrier known in the art. Preferably, the carrier is a pharmaceutically acceptable carrier. With respect to pharmaceutical compositions, the carrier can be any of those conventionally used and is limited only by factors, such as, for example, chemico-physical considerations, such as solubility and lack of reactivity with the active compound (s) and route of administration. It will be appreciated by one of skill in the art that, in addition to the following described pharmaceutical compositions, the passivated nanocrystals may be formulated as inclusion complexes, such as cyclodextrin inclusion complexes, or liposomes.

The pharmaceutically acceptable carrier may be selected based on factors including, but not limited to, the particular passivated nanocrystal and any active agent conjugated thereto, route of administration, location of the target, and/or the time course of delivery. A variety of aqueous carriers may be used, for example, (water, buffered water, isotonic saline, dextrose and the like). For example, a concentrated sucrose solution may be aseptically added to the sterile nanoparticle suspension to produce a pharmaceutical formulation. The sucrose serves as a cryoprotectant and a tonicity agent. Such a solution may be aseptically diluted to the desired concentration.

The compositions of the invention can be administered by any suitable route. Accordingly, there are a variety of suitable formulations of the pharmaceutical composition of the present inventive methods. The following formulations for oral, aerosol, parenteral, subcutaneous, intravenous, intramuscular, interperitoneal, rectal, and vaginal administration are exemplary and are in no way limiting. One skilled in the art will appreciate that these routes of administering the passivated nanocrystals of the present invention are known, and, although more than one route can be used to administer a particular passivated nanocrystal, a particular route of administration may provide a more immediate and more effective response relative to another route of administration.

Injectable formulations are among those pharmaceutical formulations that are preferred in accordance with the present invention. The requirements for effective pharmaceutical carriers for injectable compositions are well-known to those of ordinary skill in the art (see, e.g., Pharmaceutics and Pharmacy Practice, J. B. Lippincott Company, Philadelphia, Pa., Banker and Chalmers, eds., pages 238-250 (1982), and ASEP Handbook on Injectable Drugs, Toissel, 4th ed., pages 622-630 (1986), which is hereby incorporated by reference in its entirety).

Topical formulations are well-known to those of skill in the art. Such formulations may be utilized in the context of embodiments of the invention for application to the skin.

Formulations suitable for oral administration can consist of (a) liquid solutions, such as an effective amount of the passivated nanocrystals dispersed in a liquid carrier, such as, for example, water or saline; (b) capsules, sachets, tablets, lozenges, and troches, each containing a predetermined amount of active ingredient; (c) powders; (d) passivated nanocrystals suspended in a liquid carrier; and (e) emulsions. In some embodiments, liquid formulations may include diluents, such as water or alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, colorants, diluents, buffering agents, disintegrating agents, moistening agents, preservatives, flavoring agents, and pharmacologically compatible excipients. Lozenge forms can comprise the active ingredient in a flavored material, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The passivated nanocrystals prepared according to embodiments of the invention, alone or in combination with other suitable components, can be made into aerosol formulations to be administered via inhalation. These aerosol formulations can be placed into pressurized propellants, such as dichlorodifluoromethane, propane, nitrogen, and the like. In other embodiments, the passivated nanocrystals may be formulated as pharmaceuticals for non-pressured preparations, such as in a nebulizer or an atomizer.

In other embodiments, the compositions of the present invention may be administered parenterally. Typically, this will comprise the passivated nanocrystals dispersed or suspended in a pharmaceutically acceptable carrier. The term "parenteral", as used herein, means intravenous, intra-arterial, intramuscular, intra-peritoneal and to the extent feasible, intra-abdominal and subcutaneous. Pharmaceutically acceptable carriers suitable for parenteral administration include aqueous and non-aqueous liquids, isotonic sterile injection solutions, which may contain anti-oxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives. In certain embodiments, the passivated nanocrystals can be administered parenterally in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils that may be used in parenteral formulations include, for example, petroleum, animal, vegetable, or synthetic oils. Specific examples of oils include peanut, soybean, sesame, cottonseed, corn, olive, petrolatum, and mineral, to name a few. Suitable fatty acids for use in parenteral formulations include, for example, oleic acid, stearic acid, and isostearic acid. Ethyl oleate and isopropyl myristate are non-limiting examples of suitable fatty acid esters.

Soaps for use in parenteral formulations of embodiments of the invention include, for example, fatty alkali metal, ammonium, and triethanolamine salts, and suitable detergents include cationic detergents such as, for example, dimethyl dialkyl ammonium halides, and alkyl pyridinium halides, anionic detergents such as, for example, alkyl, aryl, and olefin sulfonates, alkyl, olefin, ether, and monoglyceride sulfates, and sulfosuccinates, nonionic detergents such as, for example, fatty amine oxides, fatty acid alkanolamides, and polyoxyethylenepolypropylene copolymers, amphoteric detergents such as, for example, allyl-b-aminopropionates, and 2-alkyl-imidazoline quaternary ammonium salts, and mixtures thereof.

In some embodiments, the parenteral formulations may contain preservatives and/or buffers. Additionally, in order to minimize or eliminate irritation at the site of injection, the parenteral compositions of embodiments of the invention may contain one or more nonionic surfactants. For example, in some embodiments, a non-ionic surfactant having a hydrophile-lipophile balance (HLB) of from about 12 to about 17 may be included in the parenteral formulation. The quantity of surfactant in such formulation will typically range from about 5% to about 15% by weight. Suitable surfactants may include, for example, polyethylene sorbitan fatty acid esters, such as sorbitan monooleate and the high molecular weight adducts of ethylene oxide with a hydrophobic base, formed by the condensation of propylene oxide with propylene glycol. The parenteral formulations of certain embodiments may be presented in unit-dose or multi-dose sealed containers, such as ampoules and vials, and can be stored in a freeze-dried (lyophilized) condition requiring only the addition of the sterile liquid excipient, for example, water, for injections, immediately prior to use.

Additionally, the passivated nanocrystals prepared according to embodiments of the invention, or compositions comprising such compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

In still other embodiments, the passivated nanocrystals may be administered in the presence of an agent(s) or other suitable component(s) that enhances efficacy, such as those that can further protect the passivated nanocrystals and/or active agent(s) coupled thereto from degradation or those that can prevent rapid capture by the reticuloendothelial system (RES). One such component is poly(ethylene glycol) (PEG) or PEG containing surfactants. Addition of PEG and PEG-containing copolymers to the surface of the passivated nanoparticles can result in an increase in the blood circulation half-life of the nanoparticles by several orders of magnitude.

The amount of nanoparticles or pharmaceutical compositions administered to a patient may vary and may depend on the body weight, age, and health of the patient, the size and structure of the passivated nanocrystals to be delivered, the disease being treated or imaged, and the location of diseased tissue. The term "diseased tissue", as used herein, refers to tissue or cells associated with solid tumor cancers of any type, such as bone, lung, vascular, neuronal, colon, ovarian, breast and prostate cancer. The term diseased tissue may also refer to tissue or cells of the immune system, such as tissue or cells effected by AIDS; pathogen-borne diseases, which can be bacterial, viral, parasitic, or fungal, examples of pathogen-borne diseases include HIV, tuberculosis and malaria; hormone-related diseases, such as obesity; vascular system diseases; central nervous system diseases, such as multiple sclerosis; and undesirable matter, such as adverse angiogenesis, restenosis amyloidosis, toxins, reaction-by-products associated with organ transplants, and other abnormal cell or tissue growth. Moreover, the dosage may vary depending on the mode of administration.

In order that the invention disclosed herein may be more efficiently understood, the following examples are provided. These examples are for illustrative purposes only and are not to be construed as limiting the invention in any manner.

Example 1

Passivated Alloy-Gradient Nanocrystal Preparation

Passivated CdZnSSe nanocrystals were fabricated as follows. To a 100 ml three-neck round bottom flask, 0.16 mmol of CdO, 0.4 mmol of Zn(AC)2, 200 µl of oleic acid and 8 ml of octadecene were added. The flask was connected to a vacuum and degassed for about 10 minutes, then filled with high purity nitrogen, heated up to 300° C., and stirred until a colorless solution was formed. Stock solution of sulfur and selenium were prepared in a glovebox filled with 99.999% nitrogen. Selenium powder (1.00 g) was mixed with tributylphosphine (10.00 ml) and sulfur powder (0.05 g) was mixed with octadecene (25.00 ml). An amount of the above sulfur and selenium stock solutions were mixed together in a glass vial and diluted with octadecene up to 4 ml resulting in a solution herein called an injection solution. The amount of sulfur and selenium was 1 mmol in total, the S to Se ratio was determined by the final emission wavelength of the derived nanocrystals. The injection solution was removed from the glovebox using a syringe and injected into the Cd and Zn precursor solution quickly while the growth temperature was raised to 270° C. This temperature was maintained for 40 to 60 minutes to allow the nanocrystals to grow to the desired size as determined by the desired emission wavelength.

In the glovebox, a solution was prepared for use in the deposition of one or more layers of ZnS onto the prepared nanocrystals. When no change in emission wavelength was observed of the above-prepared nanocrystals, the solution was injected slowly into the nanocrystal solution. This injection process lasted approximately two minutes.

The resultant solution was added to a 50 ml conical centrifuge tube and 5 ml hexanes and 15 ml of butanol were added. After sonication for about 1 minute, 20 ml methanol was added. The nanocrystals were centrifuged and the supernatant was discarded. The nanocrystals were washed two more times with 10 ml of hexanes, precipitated with 20 ml of methanol and re-centrifuged. The purified nanocrystals were suspended in hexanes for further capping.

The purified nanocrystals were transferred to a three-neck round bottom flask and hexanes were removed by vacuum. Trioctylphosphine oxide (8.0 g) and stearic acid (0.2 g) were added. The flask was vacuum purged for 10 minutes and heated to 100° C. for 30 minutes and then to 200° C. for 30 minutes. Capping material was prepared in a glovebox as follows: 40 ul of dimethylzinc, 80 ul of hexamethyldisilathiane and 4 ml of trioctylphosphine were mixed in a glass vial and sealed with a robber stopper. The capping solution was put in a syringe, removed from the glovebox, and slowly injected into the core solution over at least 10 minutes. The resulting solution was stirred for 30 minutes at 200° C., then removed from heat and allowed to cool to room temperature. Several monolayers of aluminum were then grown on the nanocrystals and the aluminum-coated nanocrystals were allowed to slowly oxidize at 100° C. for 2-3 hours.

Example 2

Passivated Alloy-Gradient Nanocrystal Preparation

As an example of the fabrication and performance of passivated nanoparticles of one embodiment of the invention, alloy-gradient CdSSe quantum dots with ZnS shells were synthesized according to methods described in U.S. patent application Ser. No. 11/197,620, which is herein incorporated by reference in its entirety to the extent such reference is not inconsistent with the explicit teachings of this specification. Several monolayers of aluminum were grown on the nanocrystals and the aluminum-coated nanocrystals were allowed to slowly oxidize at 100° C. for 2-3 hours.

Example 3

Fluorescence Characterization

The $Al_2O_3$-coated alloy-gradient quantum dots were incorporated into poly(methyl methacrylate) (PMMA) dissolved in toluene. The passivated quantum dot composition was then spun onto a microscope slide in a thin (~1 μm) layer and allowed to dry at room temperature. As a control, alloy-gradient quantum dots of the same design, but without an $Al_2O_3$ outer coating were also fabricated and incorporated into PMMA dissolved in toluene. Similarly, the unpassivated quantum dot composition was then spun onto a microscope slide in a thin (~1 μm) layer and allowed to dry at room temperature.

The microscope slides were placed on a custom slide holder and fluorescence spectra measurements were taken using a Shimadzu RF-5301 Spectrofluorophotometer (Shimadzu Scientific Instruments, Columbia, Md.). The Shimadzu RF-5301 Spectrofluorophotometer was configured to detect both the Rayleigh-scattered excitation light to serve as a reference and the quantum dot emission. The excitation wavelength was set to 350 nm. The excitation normalized Shimadzu RF-5301 Spectrofluorophotometer output values were then plotted as a function of wavelength (nm).

Figure 1B:
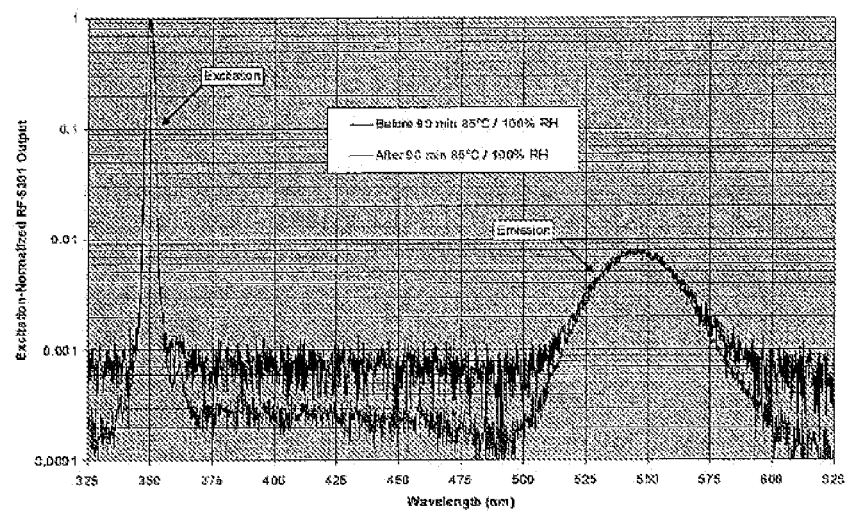
FIG. 1B is a log-scale excitation-normalized emission spectra of the passivated nanocrystals of one embodiment of the present invention.

FIG. 1A is a log-scale excitation-normalized emission spectra of the unpassivated alloy-gradient quantum dots, while FIG. 1B is a log-scale excitation-normalized emission spectra of the $Al_2O_3$-coated alloy-gradient quantum dots. As shown in FIG. 1B, the $Al_2O_3$-coated quantum dots exhibited no reduction in fluorescence and no shift in output wavelength. In comparison, as shown in FIG. 1A, the unpassivated quantum dots suffered a four-fold reduction in fluorescence and a 10 nm blue shift. The blue shift and reduction of fluorescence are consistent with oxidation of the unpassivated quantum dots and resultant loss of efficiency.

Example 4

Accelerated Environmental Exposure Characterization

To test the assertion that the $Al_2O_3$ layer functioned to passivate the alloy-gradient core-shell quantum dots, a high-temperature, high-humidity test was designed. In this test, the microscope slides from Example 2 were individually placed film-side-up on a stainless steel oven plate into a sealed 85° C. oven that contained a beaker of distilled water and was equilibrated to achieve approximately 100% relative humidity. Each microscope slide was exposed to this environment for 90 minutes. The microscope slides where then removed from the oven and allowed to cool for 2-5 minutes.

The fluorescence characteristics of each sample were re-measured as described in Example 2 to assess the impact of the high-temperature, high-humidity environment. As shown in FIG. 1A, the unpassivated quantum dots suffered a substantial reduction in fluorescence and a significant 10 nm blue shift. Comparatively, as shown in FIG. 1B, the $Al_2O_3$-coated quantum dots showed no reduction and no shift in emission wavelength and appear to be robust against high-temperature, high-humidity exposure.

Example 5

Particle Size and Zeta Potential Characterization

Passivated alloy-gradient nanoparticles were synthesized according to methods provided in Example 1 and Example 2 and the passivated nanocrystals were functionalized with a variety of chemistries: Sample NC-540-O (Functional Group: —OH, Emission Peak (nominal): 570 nm, Emission Peak (actual): 570 nm); Sample NC-575-C (Functional Group: —COOH, Emission Peak (nominal): 575 nm, Emission Peak (actual): 575 nm); Sample NC-575-N (Functional Group: —NH₃, Emission Peak (nominal): 575 nm, Emission Peak (actual): 575 nm); and Sample NC-665-C (Functional Group: —COOH, Emission Peak (nominal): 665 nm, Emission Peak (actual): 665 nm).

Figure 2:
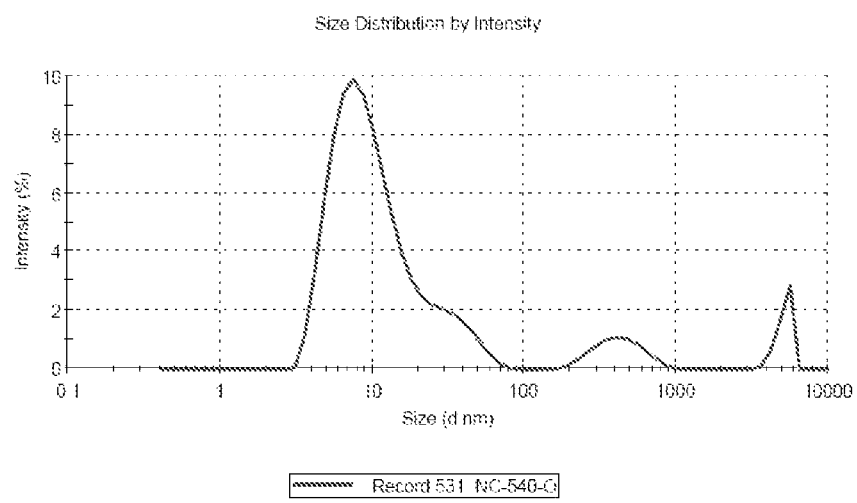
FIGS. 2-5 illustrate the particle size distribution of passivated nanocrystals of some embodiments of the invention.
Figure 3:
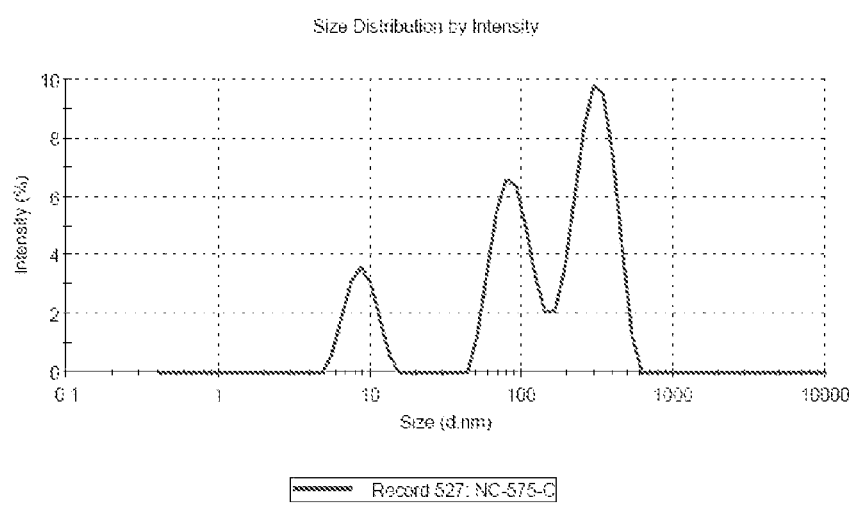
Figure 4:
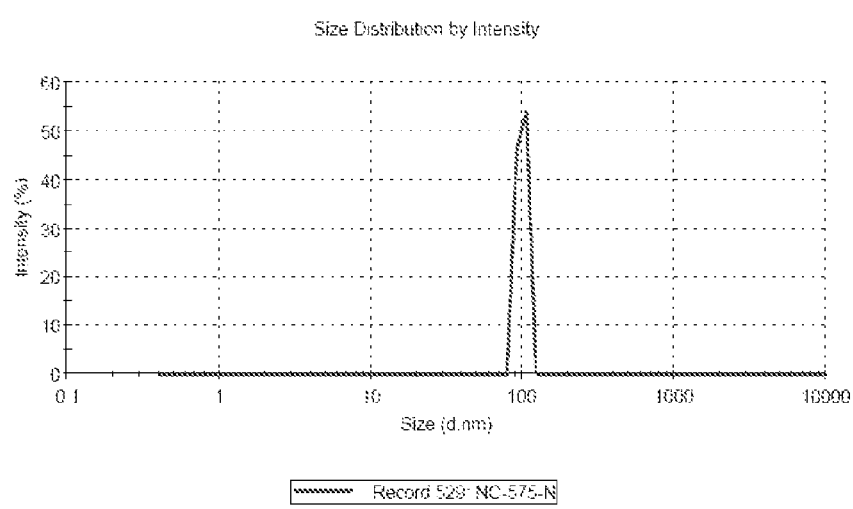
Figure 5:
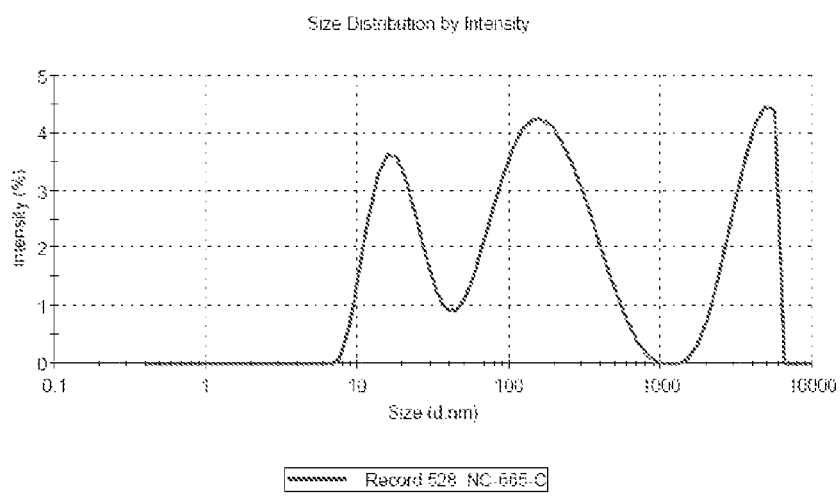

The zeta potentials of the passivated nanocrystal suspensions were measured by a Zeta PALS Analyzer based on the dynamic light scattering principle (Brookhaven Instruments Co., NY). The pH was adjusted using 0.1 M $HNO_2$ and 0.1 M KOH aqueous solutions. A Malvern Nanosizer (Malvern Instruments, UK) was used to determine the state of dispersion for the passivated nanocrystal suspensions. The particle size distribution for Sample NC-540-O (Functional Group: —OH) is shown in FIG. 2. As illustrated in FIG. 2, the passivated nanoparticles have a primary particle size of 12.7 nm in diameter. FIG. 3 shows the particle size distribution for Sample NC-575-C (Functional Group: —COOH) and a primary particle size of 8.87 nm in diameter. FIG. 4 shows the unimodal particle size distribution for Sample NC-575-N (Functional Group: —NH₃), which is indicative of a well-dispersed passivated nanocrystal suspension and stability against agglomeration. A primary particle size of 99.1 nm in diameter is provided in FIG. 4. FIG. 5 is the particle size distribution for Sample NC-665-C (Functional Group: —COOH). As illustrated in FIG. 5, the passivated nanoparticles have a primary particle size of 19.9 nm in diameter.

Example 6

Increase in Quantum Dot Fluorescence Lifetime with Passivation

Figure 6:
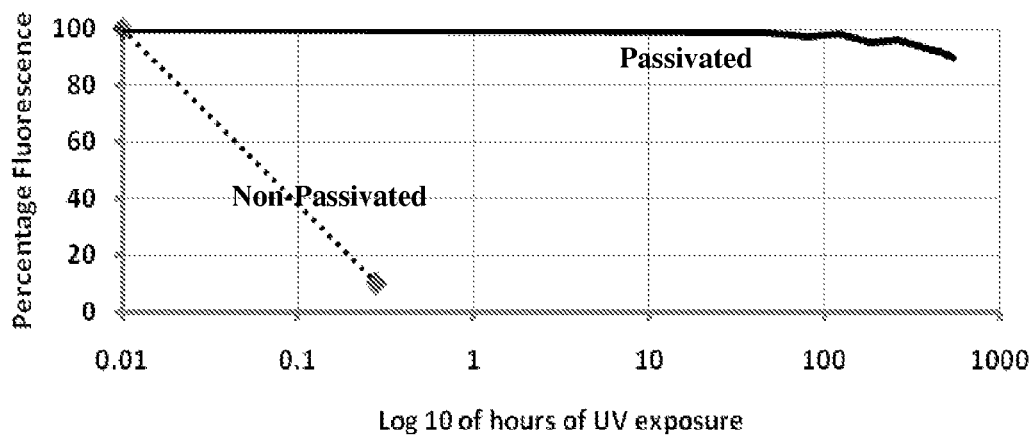
FIG. 6 is a graph depicting the comparison of the fluorescence decay of non-passivated vs. passivated quantum dots.

Compared to non-passivated quantum dots, a 20,000-fold increase in resistance to accelerated photo-thermal degradation was observed for passivated quantum dots. Both types of quantum dots were exposed to continuous high intensity UV light (25 W/cm² from a high-output mercury arc lamp) at elevated temperature (52° C.±2° C.) until their fluorescence showed 10% or more degradation. Fluorescence was monitored with a spectrometer during the tests. The fluorescence from non-passivated 515 nm quantum dots degraded to 10% of their original brightness within 17 minutes of exposure to the above conditions. A mixture of 506 nm and 626 nm passivated quantum dots under the same conditions showed less than 10% degradation over an exposure period of 550 hrs. A graph of these results appears in FIG. 6.

The foregoing description of the invention has been presented for purposes of illustration and description. It is not intended to be exhaustive or to limit the invention to the precise form disclosed, and modifications and variations are possible in light of the above teachings or may be acquired from practice of the invention. Furthermore, although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

What is claimed is:

1. A method for fabricating a passivated semiconductor nanocrystal, said method comprising the steps of:
   synthesizing an alloy-gradient nanoparticle, said nanoparticle comprising Cd, S and Se;
   applying a semiconductor coating comprising Zn and S over said alloy-gradient nanoparticle, said coating having a wider band gap than the alloy-gradient nanoparticle to provide a semiconductor coated alloy-gradient nanoparticle;
   coating the surface of the semiconductor coated alloy-gradient nanoparticle by growing monolayers of aluminum on the surface of the semiconductor coated alloy-gradient nanoparticle; and
   oxidizing the surface of said aluminum layer by exposure to an ambient environment to form an aluminum oxide layer thereon to provide a passivated semiconductor nanocrystal;
   wherein the semiconductor coated alloy-gradient nanoparticle with the aluminum oxide layer has less of a reduction in fluorescence than a semiconductor coated alloy-gradient nanoparticle not having an aluminum oxide layer.

2. The method of claim 1, wherein the semiconductor coating is a binary semiconductor coating.

3. The method of claim 1, wherein the semiconductor coating is an alloy-gradient coating further comprising at least one additional different Group VI element.

4. The method of claim 1, wherein the synthesizing step comprises dissolving the Cd, S and Se in a solvent comprising octadecene and a fatty acid to provide a nanocrystal precursor solution; and heating said precursor solution.

5. The method of claim 1, wherein the alloy-gradient nanoparticle is homogenous.

6. The method of claim 1, wherein the alloy-gradient nanoparticle is nonhomogeneous.

7. The method of claim 1, further comprising the step of coupling an active agent to the aluminum oxide layer.

8. The method of claim 7, wherein the active agent is associated with the surface of, encapsulated within, surrounded by, or dispersed throughout the passivated semiconductor nanocrystal.

9. The method of claim 7, wherein the active agent is coupled to the aluminum oxide layer.

10. The method of claim 7, wherein the active agent is selected from the group consisting of chemotherapeutic agents, diagnostic agents, imaging agents, prophylactic agents, nutraceutical agents, nucleic acids, proteins, peptides, lipids, carbohydrates, hormones, small molecules, metals, ceramics, drugs, vaccines, immunological agents, and combinations thereof.

11. The method of claim 1, further comprising the step of coupling a targeting moiety to the passivated semiconductor nanocrystal.

12. The method of claim 7, further comprising the step of coupling a targeting moiety to the active agent.

13. The method as in claim 11, wherein the targeting moiety is selected from the group consisting of a protein, peptide, antibody, antibody fragment, saccharide, carbohydrate, glycan, cytokine, chemokine, nucleotide, lectin, lipid, receptor, steroid, neurotransmitter, cell surface marker, cancer antigen, glycoprotein antigen, melanoma associated antigen, proteolytic enzyme, angiogenesis marker, prostate membrane specific antigen (PMSA), small cell lung carcinoma antigen (SCLCA), hormone receptor, tumor suppressor gene antigen, cell cycle regulator antigen, proliferation marker, human carcinoma antigen, antigen associated with an immune system disease, antigen associated with a pathogen-borne condition, and combinations thereof.

14. The method as in claim 11, wherein greater than 20% of the passivated semiconductor nanocrystal surface area is functionalized with the targeting moiety.

15. The method as in claim 11, wherein greater than 50% of the passivated semiconductor nanocrystal surface area is functionalized with the targeting moiety.

16. The method of claim 1, further comprising the step of coating said passivated semiconductor nanocrystal with an additional passivation material.

17. The method of claim 1, further comprising the step of coating said passivated semiconductor nanocrystal with a protective coating.

* * * * *